United States Patent
Welch

(10) Patent No.: US 9,005,234 B2
(45) Date of Patent: Apr. 14, 2015

(54) OCCLUSION DEVICE

(75) Inventor: Jonathan Brister Welch, Greencastle, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 451 days.

(21) Appl. No.: 13/338,762

(22) Filed: Dec. 28, 2011

(65) Prior Publication Data

US 2012/0172914 A1 Jul. 5, 2012

Related U.S. Application Data

(60) Provisional application No. 61/428,718, filed on Dec. 30, 2010.

(51) Int. Cl.
| | | |
|---|---|---|
| *A61M 29/00* | (2006.01) | |
| *A61B 17/12* | (2006.01) | |
| *A61B 19/00* | (2006.01) | |

(52) U.S. Cl.
CPC ..... *A61B 17/12022* (2013.01); *A61B 17/12109* (2013.01); *A61B 17/12136* (2013.01); *A61B 17/12172* (2013.01); *A61B 17/12186* (2013.01); *A61B 2019/4836* (2013.01)

(58) Field of Classification Search
USPC .................................. 606/191, 194, 198, 200
See application file for complete search history.

(56) References Cited

U.S. PATENT DOCUMENTS

| | | | |
|---|---|---|---|
| 4,714,460 A | 12/1987 | Calderon | |
| 4,883,459 A | 11/1989 | Calderon | |
| 4,983,166 A | 1/1991 | Yamawaki | |
| 5,072,739 A | 12/1991 | John | |
| 5,928,260 A * | 7/1999 | Chin et al. | 606/200 |
| 6,306,124 B1 | 10/2001 | Jones et al. | |
| 7,166,120 B2 * | 1/2007 | Kusleika | 606/191 |
| 2005/0101989 A1 | 5/2005 | Cully et al. | |
| 2007/0213764 A1 * | 9/2007 | Tran et al. | 606/200 |
| 2008/0058860 A1 | 3/2008 | Demond et al. | |
| 2008/0097402 A1 | 4/2008 | Hoganson et al. | |
| 2008/0215036 A1 * | 9/2008 | Vogel et al. | 604/514 |
| 2009/0264755 A1 | 10/2009 | Chen et al. | |
| 2009/0318948 A1 | 12/2009 | Linder et al. | |

\* cited by examiner

*Primary Examiner* — Tuan V Nguyen
(74) *Attorney, Agent, or Firm* — Brinks Gilson & Lione

(57) ABSTRACT

A vascular occlusion device for occluding a body cavity includes an elongate member for injecting embolization material into the body cavity and a deflecting device. The deflecting device is disposed around a distal end of the elongate member and is expandable to contact an interior wall of the body cavity in the expanded state. The deflecting device is configured to be deflected by the embolization material to change a shape of the deflecting device in the expanded state. The deflecting device provides a visual and tactile indication of completion of embolization based on the shape of the deflecting device in the expanded state.

14 Claims, 10 Drawing Sheets

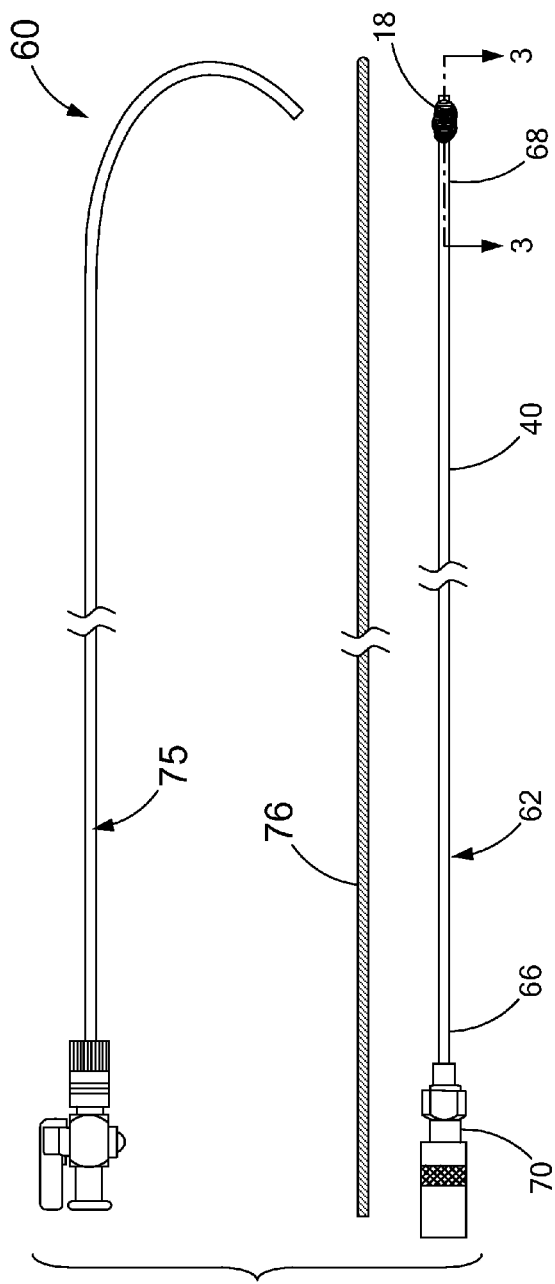
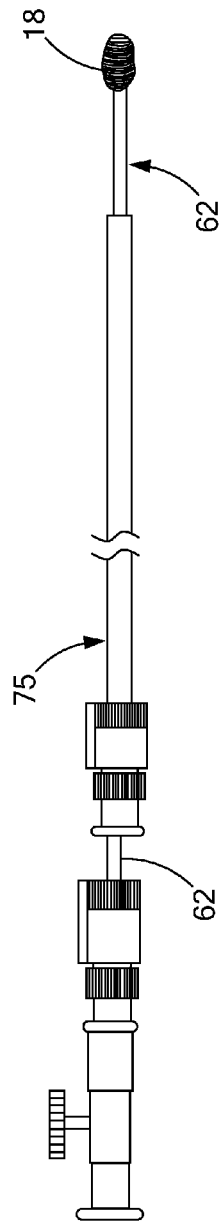

OCCLUSION DEVICE

CROSS-REFERENCE TO RELATED APPLICATIONS

This application claims the benefit of U.S. Provisional Application No. 61/428,718, filed on Dec. 30, 2011, entitled "OCCLUSION DEVICE," the entire contents of which are incorporated herein by reference.

FIELD

The present invention generally relates to medical devices, and more particularly to vascular occlusion devices.

BACKGROUND

A number of different devices may be used to occlude a body cavity including, for example, a blood vessel. An example of an occlusion device includes embolization coils. Embolization coils are permanent and promote blood clots or tissue growth over a period of time, thereby occluding the body cavity. However, while the blood clots or the tissue grows, blood may continue to flow past the coil and through the body cavity. It may take a significant period of time for sufficient tissue to grow to fully occlude the body cavity. This leaves a patient open to a risk of injury from the condition which requires the body cavity be occluded. An example of such a condition includes, but is not limited to, an atrial septal defect such as a patent foramen ovale.

When it is desirable to quickly occlude a blood vessel, an inflatable balloon may be used, and embolization material may be injected into the blood vessel. To determine the condition of embolization, an external blood pressure monitoring means is generally used.

SUMMARY

The present disclosure provides an embolization kit that provides a visual or tactile indication of condition of embolization without using an external blood pressure monitoring means.

In one form, a vascular occlusion device for occluding a body cavity includes an elongate member for injecting embolization material into the body cavity in a first direction, a deflecting device including a plurality of struts and a tubular portion. The elongate member includes a proximal end and a distal end. The plurality of struts are disposed around the distal end of the elongate member and is expandable to contact an interior wall of the body cavity in the expanded state. The tubular portion is attached to the plurality of struts and is configured to be deflected by the embolization material when the embolization material starts to flow in a second direction opposite to the first direction.

In another form, a method of occluding a body cavity includes: positioning a distal end of an occlusion device at a target site; expanding a deflecting device provided at the distal end of the occlusion device to make the deflecting device in contact with an interior wall of the body cavity; injecting embolization material into the body cavity; and determining condition of embolization based on deflection of the deflecting device by the embolization material.

Further features and advantages of the invention will become readily apparent from the following description and from the claims.

DRAWINGS

FIG. 1 is an exploded view of an embolization kit with a vascular occlusion device in accordance with an embodiment of the present disclosure;

FIG. 2 is a side view of an embolization kit with a vascular occlusion device in accordance with an embodiment of the present disclosure;

DETAILED DESCRIPTION

Figure 3:
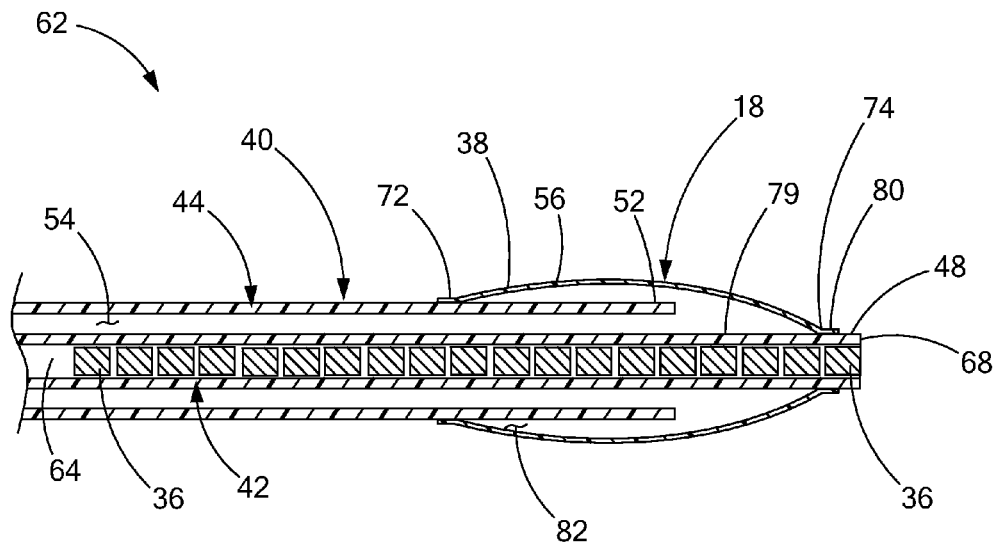
FIG. 3 is a partial, side view of a vascular occlusion device in accordance with an embodiment of the present disclosure.

Referring now to FIGS. 1 to 3, an embolization kit embodying the principles of the present disclosure is illustrated therein and designated at 60. As shown, the embolization kit 60 includes a vascular occlusion device 62 defining a proximal end 66, a distal end 68, an elongate member 40 extending from the proximal end 66 to the distal end 68, and an adaptor or hub 70 adjacent to the proximal end 66. The vascular occlusion device 62 may be a microcatheter defining a lumen and is preferably made of a soft, flexible material such as silicone or any other suitable material.

The embolization kit 60 may further include a guide catheter 75 and a guide wire 76 which provides the guide catheter 75 a path during insertion of the guide catheter 75 within a body vessel. The size of the guide wire 76 is based on the inside diameter of the guide catheter 75. In one embodiment, the guide catheter 75 is a polytetrafluoroethylene (PTFE) guide catheter or sheath for percutaneously introducing the vascular occlusion device 62 into a body vessel. Any suitable material may be used without falling beyond the scope or spirit of the present disclosure. The guide catheter 75 may have a size of about 4-8 french and allows the vascular occlusion device 62 to be inserted there through to a desired location in the body vessel.

The guide catheter 75 receives the vascular occlusion device 62 and provides stability of the vascular occlusion device 62 at a desired location within the body vessel. For example, the guide catheter 75 may stay stationary within a common visceral artery, e.g., a common hepatic artery, adding stability to the vascular occlusion device 62 as the vascular occlusion device 62 is advanced through the guide catheter 75 to a point of occlusion in a connecting artery, e.g., the left or right hepatic artery.

Figure 4:
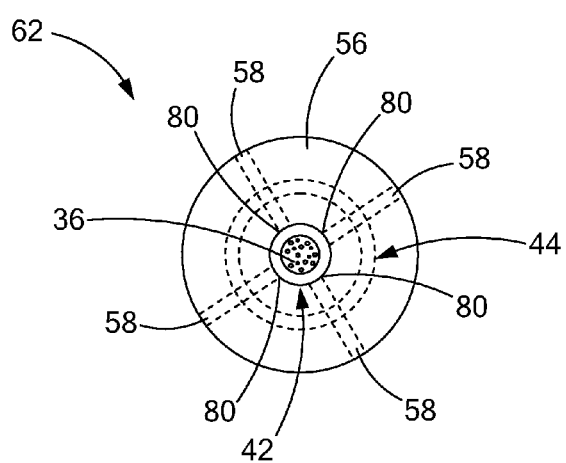
FIG. 4 is a partial, right end view of the vascular occlusion device of FIG. 3.

Referring to FIGS. 3 and 4, the vascular occlusion device 62 further includes a deflecting device 18 pivotably attached to the distal end 68 of the elongate member 40. The elongate member 40 includes an inner tubular member 42 and an outer tubular member 44 coaxially disposed around the inner tubular member 42. The inner tubular member 42 has a distal end 48. The outer tubular member 44 has a distal end 52. The distal end 48 of the inner tubular member 42 protrudes from and disposed distally from the distal end 52 of the outer tubular member 44. The inner tubular member 42 defines the occlusion lumen 64. An inflation lumen 54 is defined between the inner tubular member 42 and the outer tubular member 44.

In one embodiment, the deflecting device 18 includes a frame having a plurality of struts 58 and a tubular portion 56. The tubular portion 56 is more flexible and deflectable than the plurality of struts 58 and may be an expandable flap 56 made of an impermeable or semi-permeable material. The plurality of struts 58 define openings between adjacent ones of the struts 58. The tubular portion 56 covers the openings and prevents the embolization material from flowing through the deflecting device 18 when the deflecting device 18 is in the expanded state. The plurality of struts 58 are pivotally attached to the distal end 48 of the inner tubular member 42 and the tubular portion 56 is attached to the plurality of struts 58. The tubular portion 56 is disposed around the circumference of the distal end 48 of the inner tubular member 42 and the distal end 52 of the outer tubular member 44 and defines an interior space 82 in fluid communication with the inflation lumen 54.

The plurality of struts 58 each define a proximal end 72 and a distal end 74. The distal ends 74 are pivotably attached to an outside surface 79 of the distal end 48 of the inner tubular member 42 to form hinge points 80. The proximal ends 74 of the struts 58 are pivotable about the hinge points 80 and is expandable radially by inflation fluid from the inflation lumen 54 so that the proximal ends 72 of the struts 54 56 contact the interior walls 102 of the body vessel 100 (FIG. 5) when the deflecting device 18 is inflated. The inflation fluid may include any appropriate biocompatible fluid. When embolization is complete, the deflecting device 18 may be deflated by withdrawing the inflation fluid from the interior space 82 of the deflecting device 18 and the vascular occlusion device 62 may be removed from the patient's body. When the deflecting device 18 is in the collapsed state, the proximal ends 72 of the struts 58 contact an outer surface of the outer tubular member 44.

As an example, the plurality of struts 58 may be formed by a flexible stent wall made of nitinol. The tubular portion 56 may be made of graft materials and be an impermeable or semi-permeable structure to prevent the embolization material and the blood from flowing through the deflecting device 18 and to block backflow of the blood and embolization material.

When the distal end 68 of the vascular occlusion device 62 is at a point of occlusion in the body vessel 100, the embolization particles 36 may be loaded at the proximal end 66 via the hub 70 of the vascular occlusion device 62. In one example, saline solution is mixed with the embolization particles to form a slurry which is injected into the hub 70 of the vascular occlusion device 62 and advanced through the lumen 64. Alternatively and as illustrated in FIG. 3, the embolization particles 36 may be pre-loaded within the lumen 64 of the vascular occlusion device 62. Saline solution or other suitable transferring fluid is introduced into the lumen 64 at the proximal end 66 of the vascular occlusion device 62 to advance the embolization particles 36 to the distal end 68 of the vascular occlusion device 62.

Alternatively, a push wire (not shown) may be used to mechanically advance or push the embolization particles 36 through the vascular occlusion device 62. The size of the push wire depends on the diameter of the vascular occlusion device 62.

Figure 5:
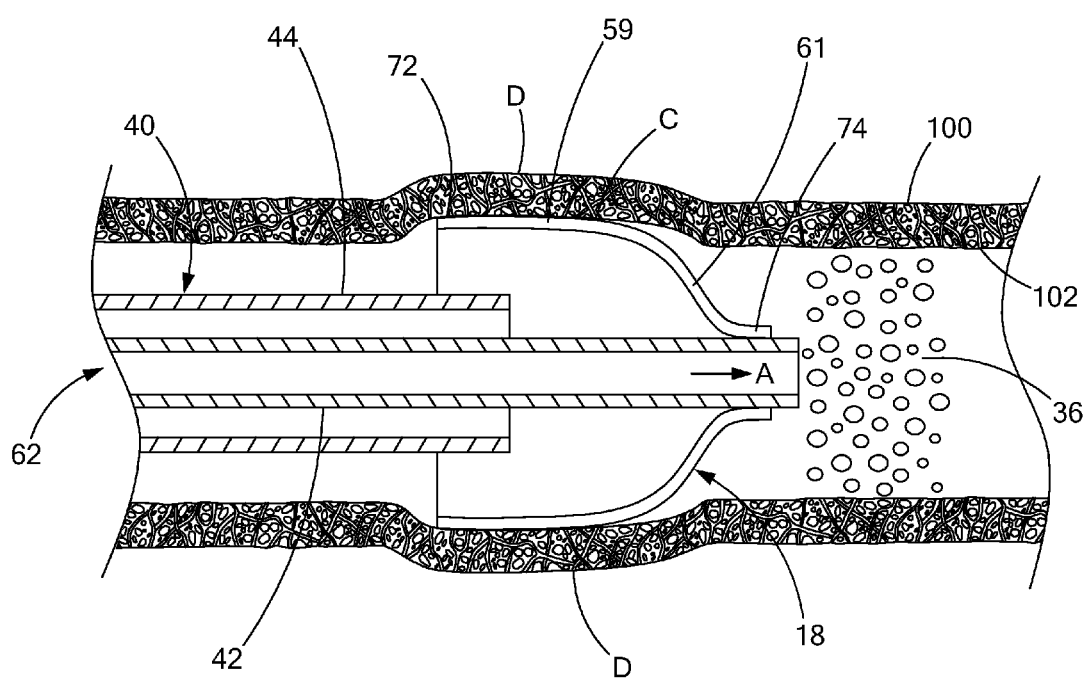
FIG. 5 is a partial, schematic environmental view of the vascular occlusion device of FIG. 3 in a blood vessel, wherein the deflecting device is in an expanded state.

Referring to FIG. 5, when the vascular occlusion device 62 is positioned at the target site, the inflation fluid is introduced through the inflation lumen 54 to the interior space 82 of the deflecting device 18 to inflate the deflecting device 18. The plurality of struts 58 are expanded radially so that the proximal ends 72 of the struts 56 contact the interior wall 102 of the body vessel 100 to help maintain the vascular occlusion device 62 at the target site. The tubular portion 56 is also expanded due to the radial expansion of the struts 58. In the expanded state, the deflecting device 18 has a configuration similar to an umbrella and defines a shape including a parallel tubular portion 59 and a tapered portion 61. The proximal ends 72 of the struts 58 are located at the parallel tubular portion 59, whereas the distal ends 74 of the struts 58 are located at the tapered portion 61. The parallel tubular portion 59 of the deflecting device 18 contact the interior wall 102 of the body vessel 100 to define a contact area C between the deflecting device 18 and the interior wall 102 of the body vessel 100. The body vessel wall is bulged by the deflecting device 18 to form a bulging area D. The tubular portion 56 may include a radiopaque material, through which the changing shape of the tubular portion 56 and consequently the changing shape of the deflecting device 18 in the process of embolization may be observed by an external imaging device (not shown). It is understood that the plurality of struts 58 may also include a radiopaque material without departing from the scope of the present disclosure.

After the deflecting device 18 is inflated from the collapsed state into the expanded state, the embolization material 36 or solution is injected into a body vessel 100, or a body cavity through the occlusion lumen 64 of the inner tubular member 42 in a first direction A to occlude the target site. The deflecting device 18 in the expanded state, particularly the tubular portion 56, blocks backflow of the blood or the embolization material 36.

Figure 6:
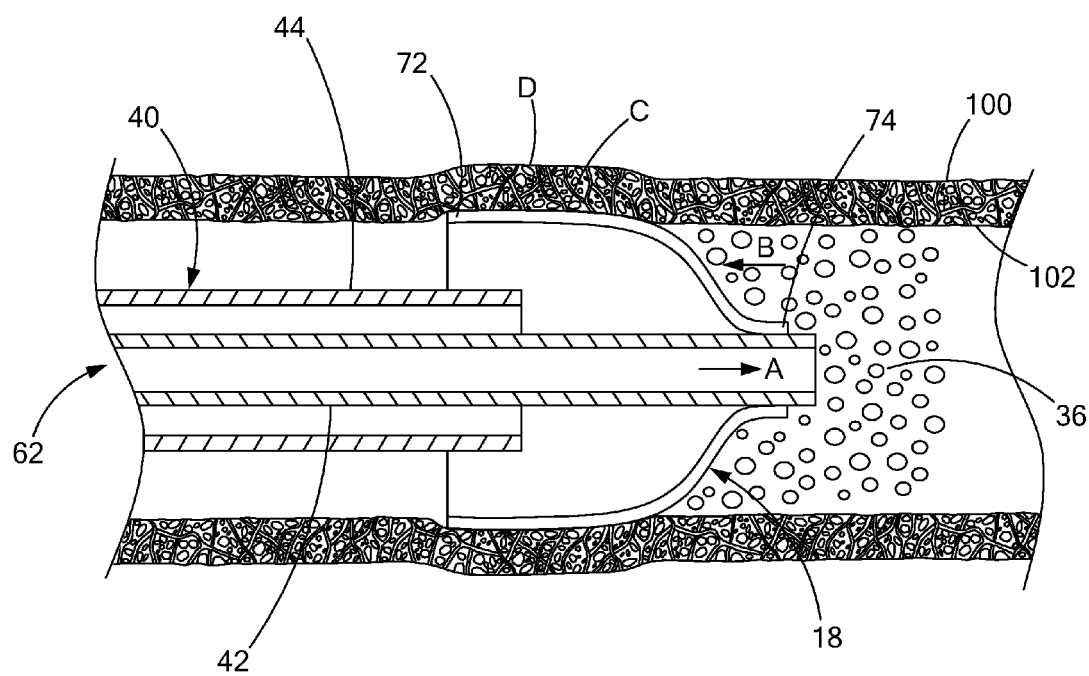
FIG. 6 is a partial, schematic environmental view of the vascular device of FIG. 3 in a blood vessel, wherein the deflecting device starts to be deflected by embolization material.

Referring to FIG. 6, as more embolization material 36 in the form of slurry is injected into the body vessel 100, the injection pressure increases. When the body vessel 100 becomes occluded, the embolization material 36 starts to flow in a second direction B opposite to the first direction A and starts to push and deflect the deflecting device 18, particularly the tubular portion 56, which is more flexible and deflectable than the struts 54. The deflection of the tubular portion 56 also causes the struts 54 to deflect. The deflecting device 18 is deflected by the embolization material into a deflected state.

Figure 7:
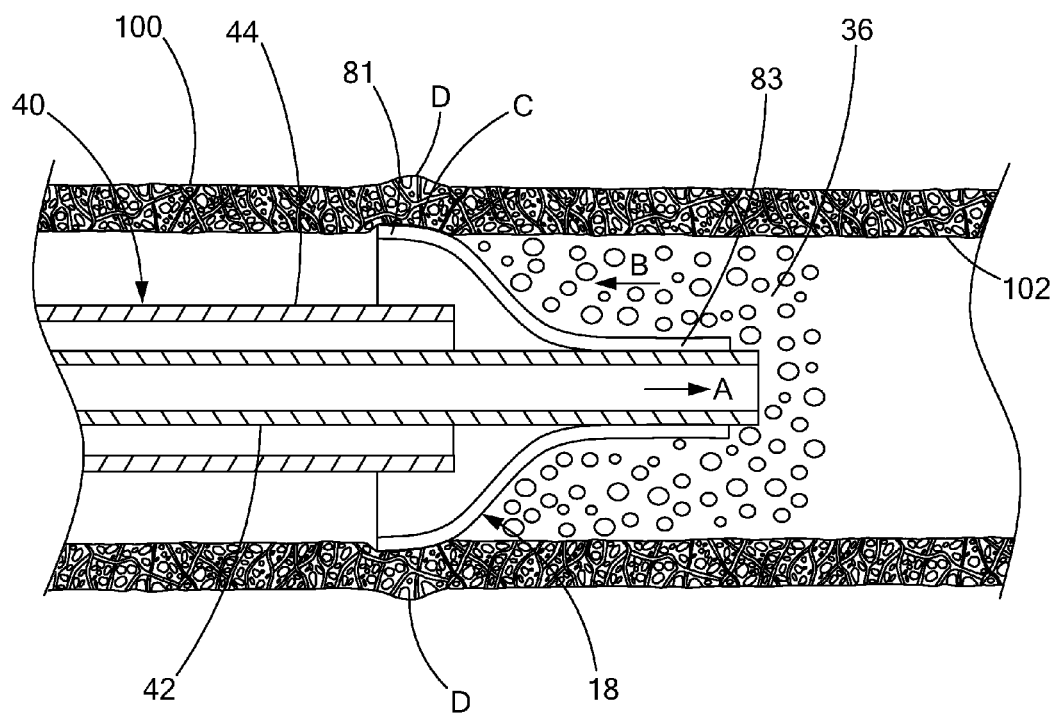
FIG. 7 is a partial, schematic environmental view of the vascular occlusion device of FIG. 3 in a blood vessel, wherein the deflecting device is deflected by embolization material into a funnel shape.

As clearly shown in FIG. 7, when the embolization material 36 flows in the second direction B, the embolization material 36 pushes the tubular portion 56 backward and deflects the tubular portion 56 and consequently the deflecting device 18 into a funnel shape having a wide portion 81 and a narrow portion 83. The proximal end of the deflecting device 18 is located at the wide portion 81, whereas the distal end of the deflecting device 18 is located at the narrow portion 83. The proximal ends of the struts 53 are flared away from the distal ends of the struts 53. The contact area C between the expandable wall and the interior wall 102 of the body vessel 100 is reduced, so does the bulging area D of the body vessel. Therefore, the changed shape of the tubular portion 58 and hence the changed shape of the deflecting device 18 indicates occurrence/degree of backflow of the embolization material. The changed shape of the tubular portion 58 may be observed by an external image device through radiological intervention.

The outside diameter of the deflecting device in the expanded state is slightly larger than the diameter of the interior wall of the body vessel. When the deflecting device is disposed in the body vessel and in the expanded state, the deflecting device bulges the body vessel walls outwardly. When the deflecting device 18 is deflected by the embolization material 36 into a funnel shape in the deflected state, the contact area C between the deflecting device 18 and the interior wall 102 of the body vessel 100 is reduced. The bulging area D of the vessel walls is also reduced. Therefore, the changed bulging area of the wall of the body vessel caused by the deflection of the deflecting device 18 provides a tactile indication of the condition of the embolization if the body vessel is located adjacent to a patient's skin. In either case, the clinician may determine whether embolization is completed based on the visual or tactile feedback without using a pressure monitoring device.

Figure 8A:
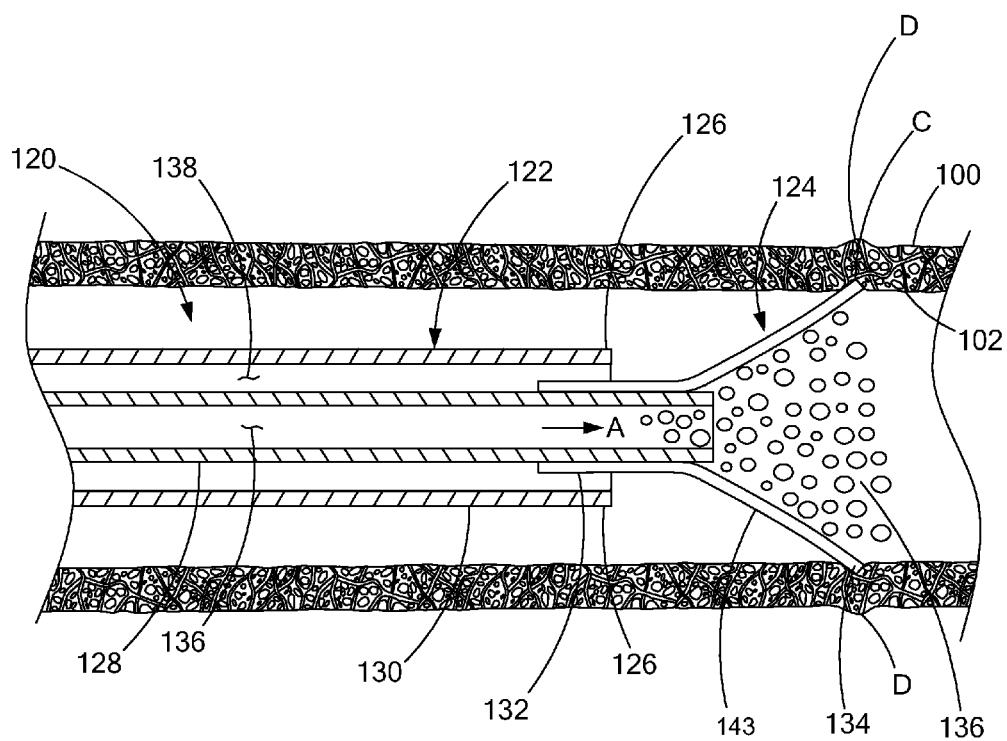
FIG. 8A is a partial, cross-sectional environmental view of an alternate form of a vascular occlusion device in a blood vessel in accordance with another embodiment of the present disclosure.
Figure 8B:
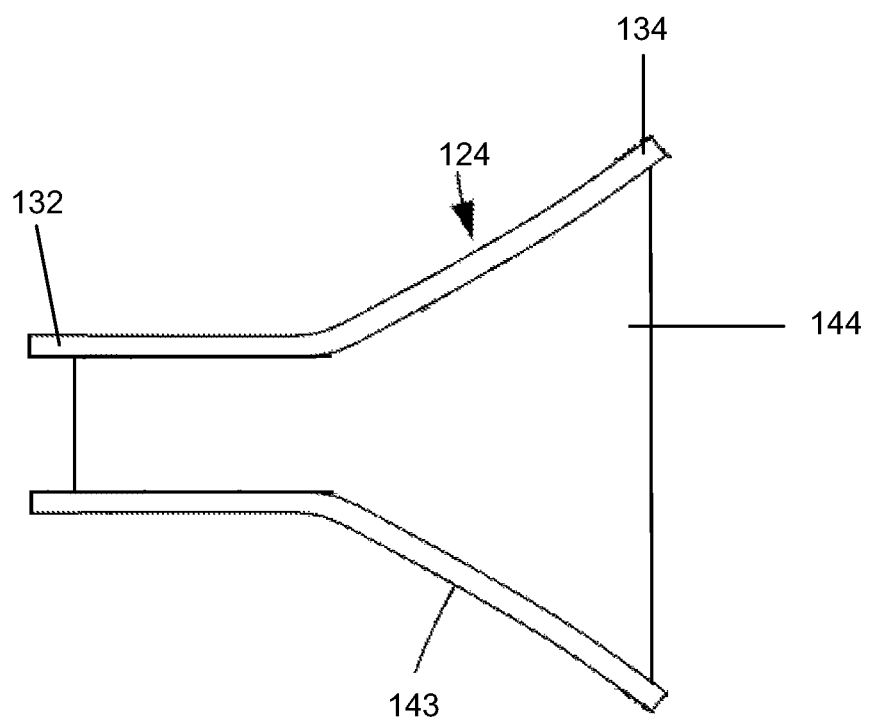
FIG. 8B is a schematic view of the vascular occlusion device of FIG. 8A.

Referring to FIGS. 8A and 8B, an alternate form of a vascular occlusion device 120 is shown to include an elongate member 122 and a deflecting device 124. The elongate member 122 defines a distal end 126 and includes an inner tubular member 128 and an outer tubular member 130 coaxially disposed around the inner tubular member 128. The deflecting device 124 includes a proximal end 132 and a distal end 134. The proximal end 132 of the deflecting device 124 is placed adjacent to the distal end 126 of the elongate member 122. The distal end 134 of the deflecting device 124 is located distally from the distal end 126 of the elongate member 122. The deflecting device 124 further includes a frame having a plurality of struts 143 and a tubular portion 144. The tubular portion 144 is attached to the plurality of struts 143 and disposed between the proximal end 132 and the distal end 134 of the deflecting device 124. The tubular portion 144 may be in the form of a flexible flap and is more flexible and deflectable than the plurality of struts 143. The tubular portion 144 covers the openings defined between adjacent ones of the struts 143 to prevent blood and embolization material from flowing backward and through the deflecting device 124. The inner tubular member 128 defines an occlusion lumen 136 through which embolization material 36 is delivered into the body vessel 100. A deployment lumen 138 is defined between the inner tubular member 128 and the outer tubular member 130 to receive the deflecting device 124 therein when the deflecting device 124 is in a collapsed state. The deflecting device 124, in the collapsed state, is received in the deployment lumen 138 when the elongate member 122 is inserted into a patient's body.

When the vascular occlusion device 120 is positioned at the target site, the deflecting device 124 is pushed outside the elongate member 122 and is expanded automatically into the expanded state. When the deflecting device 124 is deployed within the body vessel 100 or body cavity, deflecting device the distal end 134 of the deflecting device 124 engages the interior walls 102 of the body vessel 100 to maintain the deflecting device 124 in place.

The plurality of struts 143 of the deflecting device 124 may be formed by a nitinol stent configured to have a bell shape or a tapered shape in the expanded state. The proximal end 132 of the deflecting device 124 may be disposed within the outer tubular member 130 and outside the inner tubular member 132 when the deflecting device 124 is in the expanded state. The deflecting device 124, particularly the tubular portion 144, in the expanded state blocks blood flow and additionally guides the embolization material to the target site. In this embodiment, an inflation material is not needed because the plurality of struts 143 expands automatically in the deployed, expanded state. Moreover, due to the tapered shape of the tubular portion 144, the deflecting device 124 in this embodiment can be easily pulled into the outer tubular member 130 upon completion of embolization.

Figure 9:
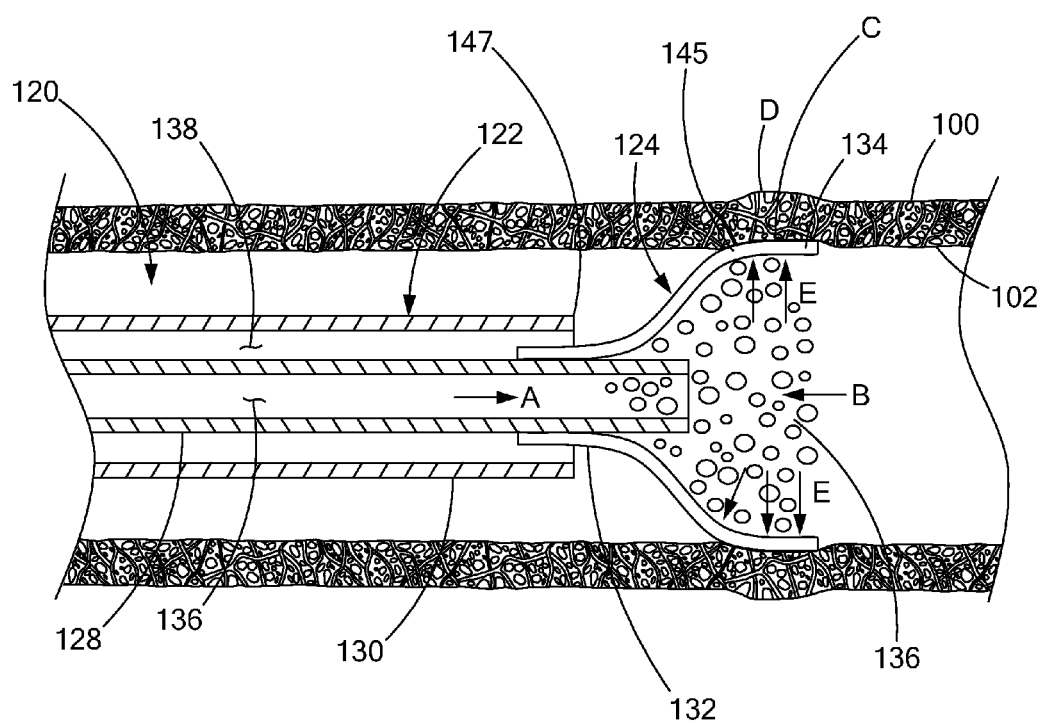
FIG. 9 is a partial, cross-sectional environmental view of the vascular occlusion device of FIG. 8A, wherein the deflecting device is deflected by embolization material into a funnel shape.

Referring to FIG. 9, after the deflecting device 124 is deployed in the body vessel 100, embolization material is injected into the target site through the occlusion lumen 136 of the vascular occlusion device 120. As the body vessel 100 becomes embolized, the injected embolization material 36 is forced backward against the elongate member 122 and the deflecting device 124. The injected embolization material 36 flowing in the reversed direction B starts to push an interior surface of the tubular portion 144 of the deflecting device 124 radially as indicated by arrow E. The shape of the tubular portion 144 and hence the shape of the deflecting device 124 is thus deflected into a funnel shape. The contact area C between the deflecting device 124 and the vessel wall 102 of the body vessel 100 is increased, thereby increasing the bulging area D of the body vessel 100. The funnel shape includes a wide portion 145 and a narrow portion 147. The proximal end 132 of the deflecting device 124 is located at the narrow portion 147, whereas the distal end 134 of the deflecting device 124 is located at the wide portion 145. The tubular portion 144 may include a radiopaque material and can be observed through radiological intervention. The deflection and the changed shape of the deflecting device 124 provides a visual indication of the condition of embolization. When the body vessel 100 is located adjacent to the skin, the changed bulging area D of the body vessel 100 caused by the deflecting device 124 may provide a tactile indication of the condition of embolization. Therefore, the clinician may determine embolization is completed when the deflecting device 124 is deflected into a funnel shape or when the shape of the deflecting device 124 starts to change, or a shape in between.

Figure 10:
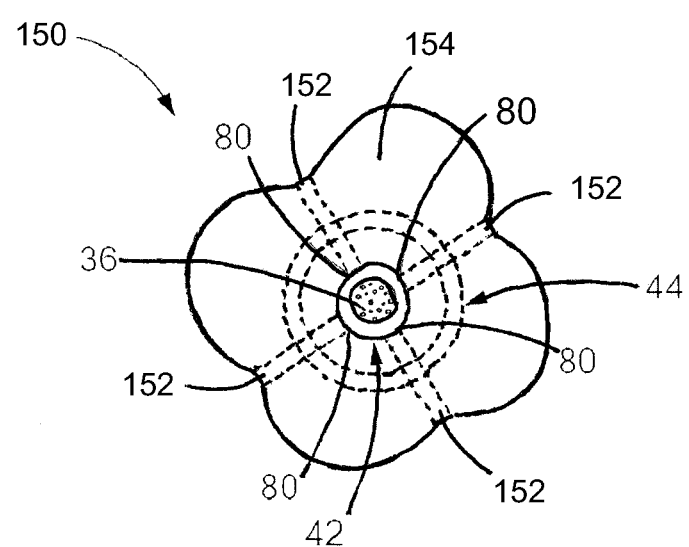
FIG. 10 is a partial, right end view of another alternate form of a deflecting device in accordance with the teachings of the present disclosure.
Figure 11:
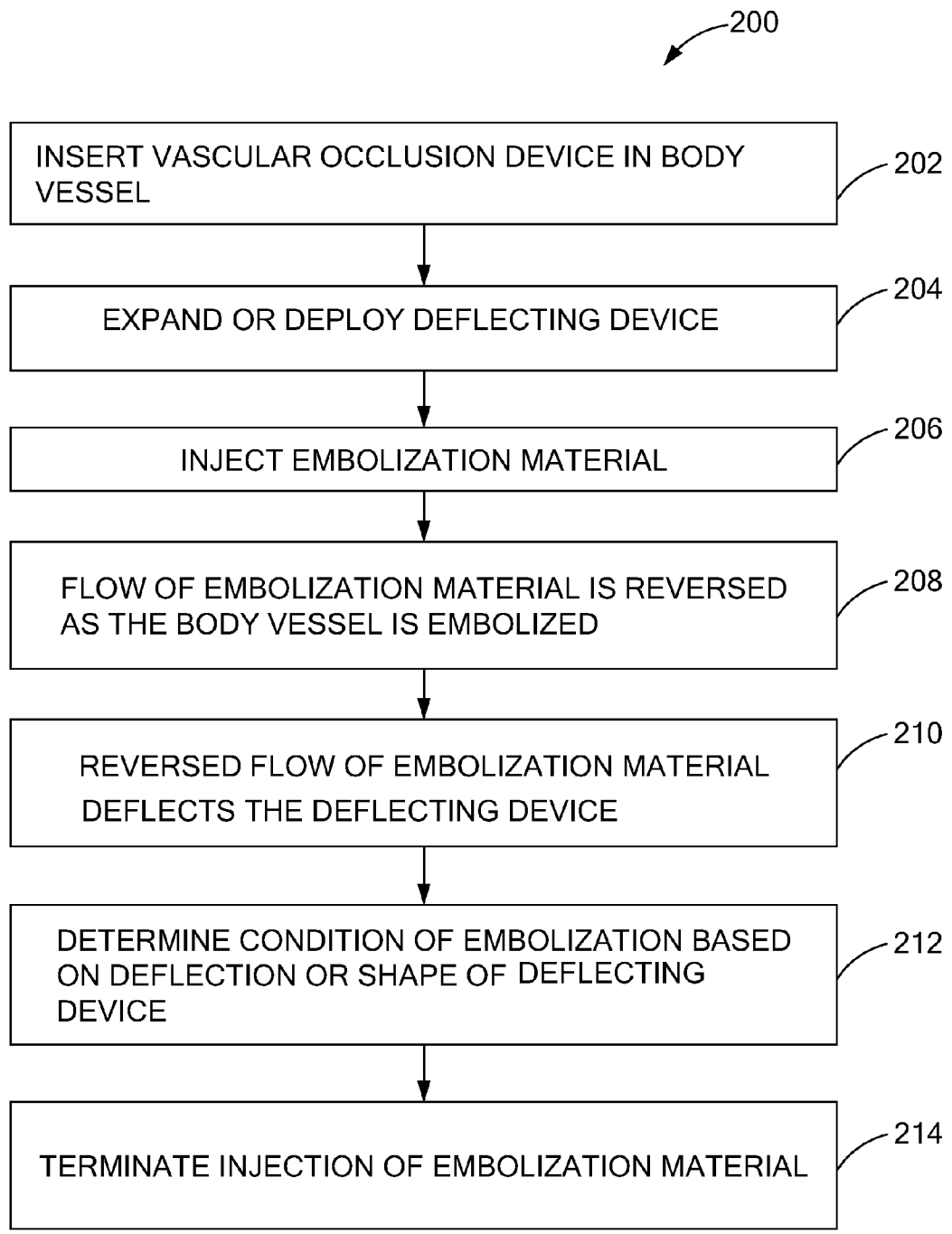
FIG. 11 is a flowchart illustrating a method of occluding a body cavity in accordance with the teachings of the present disclosure.

Referring to FIG. 10, another form of the deflecting device 150 is similar to the deflecting device 124 of FIGS. 8A, 8B and 9 except that the struts are not deflected by the embolization material. More specifically, the deflecting device 150 includes a plurality of struts 152 and a tubular portion 154 attached to the plurality of struts 152. The plurality of struts 152 are automatically expanded when deployed in the blood vessel and may have sufficient stiffness to resist deflection by the embolization material. The tubular portion 104 is made of flexible material and is deflectable by the embolization material. Therefore, when the embolization material flows in a reverse direction, the embolization material deflects the tubular portion 154 to bulge outwardly through the openings between adjacent ones of the struts 152. The radial position of the struts 152 may be slightly changed or unchanged. As a result, when the embolization material flows in a reverse direction, the deflecting device 150 is deflected into a shape having a spline cross-section. Similarly, the tubular portion 154 includes a radioopaque material, through which the changed shape of the tubular portion 154 may be observed.

It is to be understood that the embolization kit 60 described above is merely exemplary and that other kits, assemblies, and systems may be used to deploy any embodiment of the embolization particles without falling beyond the scope or spirit of the present invention. For example, a vascular occlusion device having two lumens may be used, wherein a first lumen is used to advance the embolization particles, and a second lumen allows the vascular occlusion device to be advanced along a guidewire to a desired point of occlusion.

Referring to FIG. 10, a method 200 of occluding a body cavity in accordance with the teachings of the present disclosure is described. The vascular occlusion device 62 is inserted in a body vessel 100 in step 202. The deflecting device 18, 124, 150 is expanded or deployed in the body vessel 100 after the distal end of the vascular occlusion device 18 or 124 is positioned at the target site of the body vessel in step 204. Embolization material 36 is injected into the body vessel 100 in step 206. The injection pressure increases as more embolization material is injected. When the body vessel 100 becomes embolized, the injected embolization material 36 in the form of fluid or slurry starts to flow in a reverse direction toward the deflecting device 18, 124 or 150 in step 208. The deflecting device 18, 124 or 150 is deflected by the injected embolization material 36 in step 210. The deflection of the deflecting device results in the changed shape of the deflecting device 18, 124 or 150 and the changed bulging area D of the body vessel 100. The clinician then determines the condition of embolization based on deflection or shape of the deflecting device 18, 124 or 150 or bulging area D of the body vessel 100 in step 212. The clinician then terminates injection of the embolization material 36 to complete the embolization procedure in step 214.

It is understood that the assembly described above is merely one example of an assembly that may be used to deploy the occlusion device in a body vessel. Of course, other apparatus, assemblies and systems may be used to deploy any embodiment of the occlusion device without falling beyond the scope of the following claims.

The invention claimed is:

1. A vascular occlusion device for occluding a body cavity comprising:
    an elongate member including a proximal end and a distal end, embolization material being injected into the body cavity in a first direction through the distal end of the elongate member; and
    a deflecting device movable between a collapsed state and an expanded state, the deflecting device including
    a plurality of struts attached to the distal end of the elongated member and being expandable to contact an interior wall of the body cavity in the expanded state, the plurality of struts defining openings between adjacent ones of the struts;
    a tubular portion attached to the plurality of struts to cover the openings and configured to prevent the embolization material from flowing through the deflecting device when the deflecting device is in the expanded state and configured to be deflected by the embolization material such that the deflecting device is further movable from the expanded state to a deflected state by the embolization material when the embolization material flows in a second direction opposite to the first direction,
    wherein the elongate member includes an inner tubular member defining the occlusion lumen and an outer tubular member surrounding the inner tubular member, the inner tubular member extending distally from a distal end of the outer tubular member, each of the struts including a distal end pivotally attached to a distal end of the inner tubular member and a proximal end disposed proximally from the distal end of the inner tubular member and outside the outer tubular member, and wherein when the deflecting device is in the expanded state each of the proximal ends of the struts is moved away from the outer surface of the outer tubular member.

2. The occlusion device of claim 1, wherein the tubular portion includes a radiopaque material and provides a visual indication of completion of embolization based on a shape of the tubular portion in the deflected state.

3. The occlusion device of claim 1, wherein the tubular portion is more flexible than the struts.

4. The occlusion device of claim 1, wherein the tubular portion defines a tubular shape and an inner space when the deflecting device is in the expanded state, the tubular portion surrounding the distal end of the outer tubular member.

5. The occlusion device of claim 4, wherein the inner tubular member and the outer tubular member define an inflation lumen therebetween, the inflation lumen in fluid communication with the interior space of the tubular portion.

6. The occlusion device of claim 4, wherein the deflecting device in inflated into the expanded state through an inflation material flowing from the inflation lumen to the interior space of the deflecting device.

7. The occlusion device of claim 1, wherein the proximal ends of the struts are in contact with an outer surface of the outer tubular member when the deflecting device is in the collapsed state.

8. The occlusion device of claim 1, wherein the deflecting device is deflected into a funnel shape in the deflected state.

9. The device of claim 1, wherein the outer tubular member has a continuous cross-section at its distal end, and the proximal ends of the struts contact the outer tubular member at a point proximal to the distal end of the outer tubular member.

10. The device of claim 1, wherein the deflecting device has a proximal end and a distal end, wherein the proximal end is disposed proximally of the distal end of the outer tubular member and contacts the outer tubular member on an outer surface of the outer tubular member at a point proximal to the distal end of the outer tubular member.

11. A vascular occlusion device for occluding a body cavity comprising:
    an inner tubular member defining an occlusion lumen and a distal end, embolization material being injected into the body cavity in a first direction through the occlusion lumen;
    an outer tubular member surrounding the inner tubular member and defining a distal end and an inflation lumen between the inner tubular member and the outer tubular member, the distal end of the inner tubular member being disposed distally from the distal end of the outer tubular member;
    a plurality of struts each including a distal end and a proximal end, the distal ends of the struts being attached to the distal end of the inner tubular member, the proximal ends of the struts disposed proximally from the distal end of the inner tubular member and outside the outer tubular member and contacting an outer surface of the outer tubular member at a point proximal to the distal end of the outer tubular member, the plurality of struts defining openings between adjacent ones of the struts, the plurality of struts movable between a collapsed state and an expanded state, wherein in the expanded state each of the proximal ends of the struts is moved away from the outer surface of the outer tubular member; and
    a tubular portion attached to the plurality of struts to cover the openings between adjacent ones of the struts and defining a tubular shape and an interior space in fluid communication with the inflation lumen, wherein in the expanded state the tubular portion configured to prevent the embolization material from flowing through the deflecting device and configured to be deflected by the embolization material into a deflected state when the embolization material flows in a second direction opposite to the first direction.

12. The device of claim 11, wherein the outer tubular member has a continuous cross-section at its distal end, and the proximal ends of the struts contact the outer tubular member at a point proximal to the distal end of the outer tubular member.

13. A vascular occlusion device for occluding a body cavity, comprising:
   an inner tubular member defining an occlusion lumen and a distal end, embolization material being injected into the body cavity in a first direction through the occlusion lumen;
   an outer tubular member surrounding the inner tubular member and defining a distal end and an inflation lumen between the inner tubular member and the outer tubular member, the distal end of the inner tubular member being disposed distally from the distal end of the outer tubular member;
   a plurality of struts each including a distal end and a proximal end, the distal ends of the struts being fixedly attached to the distal end of the inner tubular member, the proximal ends of the struts disposed proximally from the distal end of the inner tubular member and outside the outer tubular member and being unattached to the outer tubular member, the plurality of struts defining openings between adjacent ones of the struts, the plurality of struts movable between a collapsed state and an expanded state; and
   a tubular portion attached to the plurality of struts to cover the openings between adjacent ones of the struts and defining a tubular shape and an interior space in fluid communication with the inflation lumen, wherein in the expanded state the tubular portion configured to prevent the embolization material from flowing through the deflecting device and configured to be deflected by the embolization material into a deflected state when the embolization material flows in a second direction opposite to the first direction.

14. The device of claim 13, wherein the outer tubular member has a continuous cross-section at its distal end, and the proximal ends of the struts contact the outer tubular member at a point proximal to the distal end of the outer tubular member.

* * * * *